(12) United States Patent
Cocolas et al.

(10) Patent No.: US 9,566,248 B2
(45) Date of Patent: Feb. 14, 2017

(54) ENCASED-PELLET TABLETS

(71) Applicant: R.P. Scherer Technologies, LLC, Las Vegas, NV (US)

(72) Inventors: Harry G. Cocolas, Richmond, KY (US); Christin P. Hollis, Richmond, KY (US)

(73) Assignee: R.P. Scherer Technologies, LLC, Las Vegas, NV (US)

( * ) Notice: Subject to any disclaimer, the term of this patent is extended or adjusted under 35 U.S.C. 154(b) by 0 days.

(21) Appl. No.: 14/484,754

(22) Filed: Sep. 12, 2014

(65) Prior Publication Data

US 2015/0079167 A1 Mar. 19, 2015

Related U.S. Application Data

(60) Provisional application No. 61/877,786, filed on Sep. 13, 2013.

(51) Int. Cl.
*A61K 9/20* (2006.01)
*A61K 9/50* (2006.01)

(52) U.S. Cl.
CPC .......... *A61K 9/5031* (2013.01); *A61K 9/2031* (2013.01); *A61K 9/2081* (2013.01); *A61K 9/2095* (2013.01); *A61K 9/5089* (2013.01)

(58) Field of Classification Search
None
See application file for complete search history.

(56) References Cited

U.S. PATENT DOCUMENTS

| | | | |
|---|---|---|---|
| 5,288,501 A | 2/1994 | Nurnberg et al. | |
| 5,780,055 A | 7/1998 | Habib et al. | |
| 6,599,284 B2 * | 7/2003 | Faour .................. | A61K 9/0004 604/890.1 |
| 6,923,984 B1 | 8/2005 | Remon | |
| 7,581,941 B2 | 9/2009 | Harada et al. | |
| 2005/0152976 A1 | 7/2005 | Chenevier et al. | |
| 2009/0068263 A1 | 3/2009 | Antarkar et al. | |
| 2009/0232885 A1 * | 9/2009 | Venkatesh ............ | A61K 9/1617 424/455 |
| 2010/0092549 A1 * | 4/2010 | Blundell .............. | A61K 9/2072 424/456 |
| 2010/0209506 A1 * | 8/2010 | Eisenreich ........... | A61K 31/522 424/474 |
| 2011/0165238 A1 | 7/2011 | Liu et al. | |
| 2011/0177165 A1 | 7/2011 | Gerber et al. | |

FOREIGN PATENT DOCUMENTS

| | | |
|---|---|---|
| EP | 0355247 A2 | 2/1990 |
| EP | 0620002 A1 | 10/1994 |
| EP | 2510950 A1 | 10/2012 |
| GB | 1598458 | 9/1981 |
| WO | WO9725029 A1 | 7/1997 |
| WO | WO0050010 A1 | 8/2000 |
| WO | WO2004091582 A1 | 10/2004 |
| WO | WO2006127637 A2 | 11/2006 |
| WO | WO2008115979 A2 | 9/2008 |
| WO | WO2010064100 A1 | 6/2010 |

OTHER PUBLICATIONS

International Search Report; Mailed Dec. 23, 2014 for corresponding PCT Application No. PCT/US2014/055319.
Dwibhashyam, V., et al., "Key Formulation Variables in Tableting of Coated Pallets," Indian Journal of Pharmaceutical Sciences, 2008, vol. 70, No. 5, pp. 555-564.
Hosseini, A., et al., "Direct Compression of Cushion-Layered Ethyl Cellulose-Coated Extended Release Pellets Into Rapidly Disintegrating Tablets Without Changes in the Release Profile," International Journal of Pharmaceuticals, Jul. 25, 2013, vol. 457, pp. 503-509.
Torrado, J.J., et al., "Effect of Different Excipients on the Tableting of Coated Particle," International Journal of Pharmaceutics, 106 (1994) 149-155.
Nicklasson, F., et al., "Modulation of the tabletting behaviour of microcrystalline cellulose pellets by the incorporation of polyethylene glycol," European Journal of Pharmaceutical Sciences 9 (1999) 57-65.
Ando, M., et al., "Development and evaluation of a novel dry-coated tablet technology for pellets as a substitute for the conventional encapsulation technology," International Journal of Pharmaceutics; 336 (2007) 99-107.

* cited by examiner

*Primary Examiner* — Robert A Wax
*Assistant Examiner* — Quanglong Truong
(74) *Attorney, Agent, or Firm* — Mendolsohn Dunleavy, P.C.

(57) ABSTRACT

An encased-pellet tablet for an active pharmaceutical ingredient comprises an excipient layer on the outside and an inner core that is surrounded by the excipient layer. The inner core contains a plurality of coated pellets, and the coated pellets comprise pellets of the active pharmaceutical ingredient coated with a pellet coating. The excipient layer contains from about 1 wt. % to about 20 wt. % of at least one cushioning agent selected from polyhydroxyl compounds. A method for manufacturing the encased-pellet tablets involves compressing an excipient material to form a first layer; compressing a plurality of coated pellets containing an API on said first layer to form an inner core thereon and compressing additional excipient material around an exposed portion of said inner core thereby surrounding said inner core with excipient material.

21 Claims, 5 Drawing Sheets

ENCASED-PELLET TABLETS

BACKGROUND OF THE INVENTION

1. Field of the Invention

The present invention relates to encased-pellet tablets. In particular, the invention is directed to encased-pellet tablets with an outer layer that encompasses an inner core comprising plurality of coated pellets, and a method for making such encased-pellet tablets.

2. Description of the Related Technology

Interest in controlled release pharmaceutical dosage formulations has brought about increasing attention to delivery systems which employ multiple coated particles, like pellets, coated microgranules and microcapsules, where the coating on the particles can be used to control release of the active pharmaceutical ingredient (API). Controlled release may include delayed release, extended release, or repeated release. Capsules may be employed as a delivery platform for oral administration of these coated pellets or microcapsules. More recently, there is interest in finding ways to incorporate such coated pellets into a tablet. The advantages of encased-pellet oral tablets may include: (i) reduced cost and faster production; (ii) reduced vulnerability to tampering, (iii) less difficulties in esophageal transport than for capsules, and (iv) ease of swallowing.

Such a tablet may include pellets containing at least one API. Each of the pellets is individually coated with a polymer film that modifies the release profile and/or release rate of the API. The coated pellets are then formed into tablets by compression of a plurality of the coated pellets with excipients. In one method, the coated pellets are mixed with the excipients and this mixture is then compressed into tablets to provide an encased-pellet tablet where the coated pellets substantially homogenously distributed throughout the excipient matrix.

One problem that is encountered is that the compression step used to form the tablets will subject the coated pellets to a relatively large compression force. The pellet coating thus experiences large stresses, which often causes cracks or breaks in the pellet coating, which will alter the release profile and/or release rate of the API. Such tablets may thus lose at least some of the benefits of the controlled release properties of the coated pellets. Therefore, there is a need to preserve the pellet coating during tablet compression when making encased-pellet tablets.

One option for helping the pellet coating withstand the large force of tablet compression without being damaged is to strengthen the pellet coating. For example, GB 1 598 458 discloses a tablet comprising a micro-capsulated substance or a substance with a brittle coating, and a carrier that is a water-soluble, natural or synthetic wax having a melting temperature of at least 30° C. in an amount of more than 2% w/w and not more than 20% w/w, calculated based on the weight of the microcapsules or substance having a brittle coating. Polyethylene glycol (PEG) is mentioned as an example of a water soluble wax. Other carriers include microcrystalline cellulose and lactose. Example 2 of the patent produced tablets by mixing 940 mg of KCl microcapsules, 94 mg of microcrystalline cellulose, and 94 mg PEG 1000, among other components; and compressing the mixture to tablets. The KCl is encapsulated and then the KCl microcapsules are dispersed in a matrix of the carrier in the tablets. The weight ratio of microcrystalline cellulose and PEG in the tablets is 1:1.

WO 2000/50010 discloses a controlled release dosage form of the drug bupropion hydrochloride. The dosage form comprises: (a) a first pellet having a core of bupropion hydrochloride and hydroxypropyl methylcellulose, where the core is coated with a mixture of hydroxypropyl methylcellulose and PEG, which coated core is further coated with a mixture of an acrylic resin and a water soluble polymer; and (b) a second pellet which is formed by further coating the first pellet with hydroxypropyl methylcellulose, followed by an enteric coating. The enteric coating may include a polymer such as cellulose acetate phthalate or methacrylic acid copolymer. The first pellet and the second pellet may then be mixed with excipients such as crospovidone XL-10 and microcrystalline cellulose PH102 and then the mixture can be compressed into tablets.

EP 0 620 002 A1 discloses a solid pharmaceutical dosage form having an API core coated with a pharmaceutically acceptable polyalkylene glycol to reduce abrasion. The disclosed polyalkylenes include polyethylene, polypropylene and polybutylene. The API core may be a tablet having an abrasive type nature such that the tablet surface roughens and erodes during coating. Coating such tablets with a coating material comprising PEG is said to reduce abrasion during the coating process.

US 2005/0152976 A1 discloses a sustained-release formulation particle, which comprises an API and binder core coated with a coating film containing at least one cellulose based polymer and a plasticizer. The plasticizer may be polyethylene glycol, among a long list of plasticizers. The sustained-release formulation particles may be mixed with a combination of excipients such as a disintegrant and/or a swelling agent; at least one diluent; a lubricant; and optionally an antistatic agent, a permeabilizer, sweeteners, flavorings and colorants. The mixture may then be compressed to form tablets.

U.S. Pat. No. 6,923,984 discloses biologically inactive cushioning beads comprising at least one compressible cushioning component consisting essentially of a microcrystalline hydrocarbon wax or a natural wax, with the wax being at least 30% by weight of the biologically inactive cushioning beads. The biologically inactive cushioning beads may be used for making solid shaped articles (e.g. tablets) by mixing with biologically active ingredient-loaded beads and compressing the mixture to form solid shaped articles. The biologically active ingredient-loaded beads may be coated with a polymer and a plasticizer, among which plasticizers is PEG.

EP 2 510 950 A1 discloses a press-coated orally-disintegrating tablet with an outer layer surrounding an inner core. The inner core includes a powder or granular material with poor formability and contains an active ingredient. The outer layer comprises (a) microcrystalline cellulose, (b) a sugar or a sugar alcohol, and (c) one or more ingredients selected from crospovidone, starches, low-substituted hydroxypropylcellulose and carmellose. The inner core has a thickness in the range of 30 to 80% of the entire tablet.

U.S. Pat. No. 7,581,941 B2 discloses an apparatus for manufacturing a tablet with an inner core and an outer layer surrounding the inner core. The apparatus comprises a center punch and an outer punch surrounding the outer periphery of the center punch, both of which are slidable and capable of compressing. The apparatus also includes a relative position restriction means for restricting a relative position of the center and outer punches. The relative position restriction means is configured to restrict a first position in which a punch tip of the center punch is protruded from a punch tip of the outer punch and a second position in which the punch tip of the center punch is substantially coincident with the punch tip of the outer punch, and may be further configured to fail to restrict a third position in which the punch tip of the center punch is retracted within the punch tip of the outer punch.

Nicklasson et al. ("Modulation of the tabletting behaviour of microcrystalline cellulose pellets by the incorporation of polyethylene glycol," *European Journal of Pharmaceutical Sciences*, vol. 9, pages 57-65, 1999) teaches pellets made by wet agglomeration of microcrystalline cellulose and PEG at a 50:50 weight ratio, followed by spheronisation. The pellets are then compressed to form tablets.

The present invention provides encased-pellet tablets that can reduce the impact of tablet compression on the pellet coating while at the same time providing desirable API release characteristics that can be tailored to particular applications. Such encased-pellet tablets may significantly reduce cracking of the pellet coating during tablet compression when compared to conventional encased-pellet tablets. Therefore, the encased-pellet tablets can be fabricated to have a drug release profile that is similar to that of the coated pellets themselves.

SUMMARY OF THE INVENTION

In one aspect, the present invention is directed to an encased-pellet tablet containing an API, comprising (a) an inner core containing a plurality of coated pellets, each comprising the API coated with a pellet coating, and (b) an excipient layer formed on an outer surface of the inner core. The excipient layer contains an amount of from about 1 wt. % to about 20 wt. % of at least one cushioning agent selected from polyhydroxyl compounds, based on the weight of the excipient layer.

In another aspect, the encased-pellet tablet of the present invention has an excipient layer with at least one cushioning agent selected from polyethylene glycol, polypropylene glycols, polytetramethylene glycols, polybutylene glycols, polybutadiene diols and triols, low molecular weight hydroxy-containing polyesters, hydroxy-containing polyester amides, polyalkylene ether glycol compounds, hydroxy-containing oils and mixtures thereof.

In yet another aspect, the present invention provides a method for manufacturing an encased-pellet tablet comprising the steps of: (i) compressing an excipient material with a compression force from about 0.1 kN to 3 kN to form first layer; (ii) compressing a plurality of coated pellets containing an API with a compression force from about 0.1 kN to 3 kN to form an inner core; and (iii) compressing additional excipient material on said inner core with a compression force from 2 kN to 20 kN to thereby surround the inner core with excipient material.

DETAILED DESCRIPTION OF THE PREFERRED EMBODIMENT(S)

Figure 1:
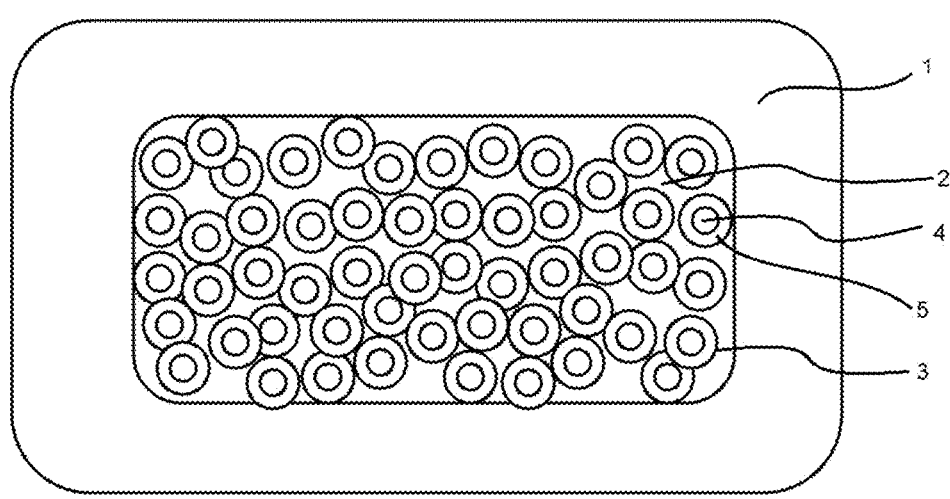
FIG. 1 is schematic representation of an encased-pellet tablet according to one embodiment of the present invention.

For illustrative purposes, the principles of the present invention are described by referencing various exemplary embodiments. Although certain embodiments of the invention are specifically described herein, one of ordinary skill in the art will readily recognize that the same principles are equally applicable to, and can be employed in other systems and methods. Before explaining the disclosed embodiments of the present invention in detail, it is to be understood that the invention is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

In one aspect, the present invention provides an encased-pellet tablet comprising an inner core 2 that is encased by an excipient layer 1. The inner core 2 contains a plurality of coated pellets 3, which comprise pellets 4 containing at least one API, and a pellet coating 5. Pellets 4 may comprise at least one API, which may either be sprayed onto a sugar-sphere core, as described in Vuppala, et al., "Application of Powder-Layering Technology and Film Coating for Manufacture of Sustained-Release Pellets Using a Rotary Fluid Bed Processor," *Drug Development and Industrial Pharmacy*, volume 23, pages 687-694, 1997, or may be subjected to an extrusion-spheronization process, as described in Dukić-Ott et al., "Production of pellets via extrusion-spheronisation without the incorporation of microcrystalline cellulose: A critical review," *European Journal of Pharmaceutics and Biopharmaceutics*, volume 71, pages 38-46, 2009.

The inner core 2 comprises plurality of coated pellets 3 that contain an API in particle form. The API may be any API suitable for oral administration. The API may be selected from, but is not limited to, gastrointestinal sedatives, antacids, analgesics, anti-inflammatories, coronary vasodilators, peripheral and cerebral vasodilators, anti-infectives, antibiotics, antiviral agents, anti-parasitic agents, anticancer agents, anxiolytics, neuroleptics, central nervous system stimulants, antidepressants, antihistamines, antidiarrheal agents, laxatives, dietary supplements, immunodepressants, hypocholesterolemiants, hormones, enzymes, antispasmodics, antianginal agents, medicinal products that affect the heart rate, medicinal products used in the treatment of arterial hypertension, antimigraine agents, medicinal products that affect blood clotting, antiepileptics, muscle relaxants, medicinal products used in the treatment of diabetes, medicinal products used in the treatment of thyroid dysfunctions, diuretics, anorexigenic agents, antiasthmatics, expectorants, antitussive agents, mucoregulators, decongestants, hypnotics, antinausea agents, hematopoietic agents, uricosuric agents, plant extracts and contrast agents.

In some embodiments, inner core 2 may comprise two or more different types of coated pellets 3, each of which may be separately and independently coated with the same pellet coating 5 or with different pellet coatings 5. In one embodiment, inner core 2 may comprise at least two different types of coated pellets 3 containing the same API, but having different release characteristics as a result of having different pellet coatings 5. One type of coated pellet may have the API coated, for example, with a film that delays API release, while another type of coated pellet may have a coating that releases the active ingredient relatively quickly. Thus, the use of particular combinations of two or more types of coated pellets 3 in inner core 2 provides the ability to tailor the release profile of the encased-pellet tablet. An advantageous duration and/or continuity of API release can thereby be achieved by the encased-pellet tablets of these embodiments.

In another embodiment, inner core 2 comprises a first type of coated pellets 3 containing a first API and a second type of coated pellets 3 containing a second, different API. In this embodiment, each type of coated pellet 3 may have the same or a different pellet coating 5. By selecting suitable pellet coatings 5, APIs otherwise incompatible with one another can be combined in one tablet to allow administration of multiple different API's in a single dosage form. Further, the release characteristics for each API may be individually tailored by selection of pellet coatings 5.

In some embodiments, inner core 2 may also comprise one or more optional components selected from cushioning agents, disintegrants, plasticizers, binders, diluents, and antistatic agents. In these embodiments, coated pellets 3 may be mixed with the optional components before being compressed to form inner core 2.

Disintegrants for the inner core 2 may be selected from sodium starch glycolate, crosslinked polyvinylpyrrolidone (crospovidone), crosslinked sodium carboxymethylstarch and crosslinked sodium carboxymethylcellulose (croscarmellose), and combinations thereof. The disintegrant may be used in the inner core 2 in conventional amounts of, for example, from about 0.5 wt. % to about 15 wt. %, based on the total weight of the inner core 2.

In some embodiments, inner core 2 may also comprise at least one cushioning agent at a weight percentage of from about 1% to about 20%, or from about 2% to about 18%, or from 4% to about 18%, or from 5% to about 15%, or from 7% to about 12%, or from about 4% to about 11%, based on the total weight of inner core 2.

The cushioning agent in inner core 2, if present, may be the same as or different from the cushioning agent in excipient layer 1. The cushioning agent may be selected from polyhydroxyl compounds, including polyoxyalkylene compounds having at least two hydroxy groups in the monomer. Examples of suitable cushioning agents include polyethylene glycols, polypropylene glycols, polytetramethylene glycols, polybutylene glycols, polybutadiene diols and triols, low molecular weight hydroxy-containing polyesters, hydroxy-containing polyester amides, polyalkylene ether glycol compounds, hydroxy-containing oils, including tongue oil and their alkyl modifications. In one embodiment, the cushioning agent in both inner core 2 and excipient layer 1 is polyethylene glycol.

A binder for use in the inner core 2 may be selected from cellulose-based polymers, acrylic polymers, povidones, copovidones, polyvinyl alcohols, alginic acid, sodium alginate, starch, pregelatinized starch, sugars and derivatives thereof, guar gum and polyethylene glycols, polyvinylpyrrolidone, gelatin, acacia, glucose, and combinations thereof. Examples of cellulose-based polymers include ethylcellulose, hydroxypropylcellulose and hydroxypropylmethylcellulose. Examples of acrylic polymers include ammoniomethacrylate copolymer, acrylic and methacrylic acid polymers and copolymers, polyacrylates and polymethacrylates.

A diluent for use in the inner core 2 may be selected from cellulose-based derivatives such as microcrystalline cellulose, and is preferably selected from microcrystalline cellulose, starches, lactose, other sugars and derivatives thereof, polyols and combinations thereof.

An antistatic agent for use in the inner core 2 may be selected from colloidal silica (such as the product sold under the brand name Aerosil®), precipitated silica (such as the product sold under the brand name Syloid® FP244), and micronized or nonmicronized talc, and combinations thereof.

The pellet coating 5 may be made up of any suitable, conventional ingredients for pellet coatings that provide the desired release characteristics for a particular API. In one embodiment, pellet coating 5 is an enteric coating. Pellet coating 5 may contain one or more conventional excipients. For example, pellet coatings may comprise a cellulose-based polymer. Examples of cellulose-based polymers are ethylcellulose, methylcellulose, hydroxypropylmethyl cellulose, cellulose acetate phthalate, polymers of methacrylic acid and methacrylic acid esters, for instance Eudragit®, and polyvinyl derivatives. The coating polymers for the pellet coating are also described in Felton et al., "An update on pharmaceutical film coating for drug delivery," *Expert Opinion on Drug Delivery*, volume 10, pages 421-435, 2013; Dashevsky et al., "Compression of pellets coated with various aqueous polymer dispersions," *International Journal of Pharmaceutics*, volume 279, pages 19-26, 2004; and Shukla et al., "Carbohydrate polymers: Applications and recent advances in delivering drugs to the colon," *Carbohydrate Polymers*, volume 88, pages 399-416, 2012; which are incorporated by reference herein in their entirety.

The pellet coating 5 can have different functions, for example, taste masking, odor masking, stabilization of the API, improving the processability, improving the flow behavior, decreasing the hygroscopicity, guaranteeing and improving the chemical and/or mechanical stability of the API, modifying the release of the API from the pellet, modifying the API bioavailability, and coloring. Modification of the release of the API may comprise, for example, causing uniformly prolonged active ingredient release, extending API release, delaying API release, repeated API release, stepped API release and any combination thereof.

Optionally, the pellet coating 5 may also comprise a plasticizer. Examples of suitable plasticizers include triethyl citrate, acetyltributyl citrate, triacetin, tributyl citrate, diethyl phthalate, polyethylene glycols, acetyl triethyl citrate, dibutyl sebacate, dibutyl phthalate, glycerine, polysorbates and mono- and diacetyl glycerides. The plasticizer can be used, for example, to lower the glass transition temperature of the pellet coating 5 and improve the mechanical properties of the pellet coating 5.

Referring to FIG. 1, excipient layer 1 is a layer surrounding or completely surrounding or encasing inner core 2. Excipient layer 1 may comprise a polymer selected from cellulose-based polymers, such as, for example, microcrystalline cellulose, ethylcellulose, methylcellulose, and hydroxypropylmethyl cellulose, polysaccharides such as lactose, cellulose acetate phthalate, polymers of methacrylic acid and methacrylic acid esters, for instance Eudragit®, and combinations thereof. In one embodiment, the excipient layer comprises a mixture of microcrystalline cellulose, lactose, disintegrant, and a cushioning agent. The coating polymers for the excipient layer are also described in Felton et al., "An update on pharmaceutical film coating for drug delivery," *Expert Opinion On Drug Delivery* volume 10, pages 421-435, 2013; Dashevsky et al., "Compression of pellets coated with various aqueous polymer dispersions," *International Journal of Pharmaceutics*, volume 279, pages 19-26, 2004; and Shukla et al., "Carbohydrate polymers: Applications and recent advances in delivering drugs to the colon," *Carbohydrate Polymers*, volume 88, pages: 399-416, 2012; which are incorporated by reference herein in their entirety.

The amount of polymer contained in the excipient layer 1 may range from about 5 wt. % to about 99 wt. %, or from about 10 wt % to about 95 wt. %, or from about 20 wt % to about 80 wt. %, based on the total weight of the excipient layer.

Excipient layer 1 also comprises at least one cushioning agent at a weight percentage of from about 1 wt. % to about 20 wt. %, or from about 2% to about 18%, or from 4% to about 18%, or from 5% to about 15%, or from 7% to about 12% or from 4% to about 11%, based on the total weight of the excipient layer 1.

The cushioning agent can provide a cushioning effect to the coated pellets 3 that will reduce the impact of tablet compression on coated pellets 3, and particularly on the pellet coating layer 5. The cushioning agent may be selected from polyhydroxyl compounds, including polyoxyalkylene compounds having at least two hydroxy groups in the monomer. Examples of suitable cushioning agents include polyethylene glycols, polypropylene glycols, polytetramethylene glycols, polybutylene glycols, polybutadiene diols and triols, low molecular weight hydroxy-containing polyesters, hydroxy-containing polyester amides, polyalkylene ether glycol compounds, hydroxy-containing oils, including tongue oil and their alkyl modifications. Suitable molecular weights for the cushioning agent are between 300 g/mol and 20,000 g/mol.

The excipient layer 1 may comprise one or more optional excipients selected from a binder, a disintegrant, a swelling agent, a diluent, a lubricant, an antistatic agent or a glidant, a permeabilizer, a sweetener, a flavoring agent and a colorant.

A binder for use in the excipient layer 1 may be selected from cellulose-based polymers, acrylic polymers, povidones, copovidones, polyvinyl alcohols, alginic acid, sodium alginate, starch, pregelatinized starch, sugars and derivatives thereof, guar gum and polyethylene glycols, polyvinylpyrrolidone, gelatin, acacia, glucose, and combinations thereof. Examples of cellulose-based polymers include ethylcellulose, hydroxypropylcellulose and hydroxypropylmethylcellulose. Examples of acrylic polymers include ammoniomethacrylate copolymer, acrylic and methacrylic acid polymers and copolymers, polyacrylates and polymethacrylates.

A disintegrant for the excipient layer 1 may be selected from sodium starch glycolate, crosslinked polyvinylpyrrolidone (crospovidone), crosslinked sodium carboxymethylstarch and crosslinked sodium carboxymethylcellulose (croscarmellose), and combinations thereof. The disintegrant may be used in conventional amounts of, for example, from about 0.5 wt. % to about 20 wt. %, or from about 1 wt. % to about 10 wt. %, or from about 4 wt. % to about 15 wt. %, or from about 3 wt. % to about 11 wt. %, based on the total weight of the excipient layer 1.

A swelling agent for the excipient layer 1 may be selected from microcrystalline celluloses, starches, modified starches, and combinations thereof.

A diluent for the excipient layer 1 may be selected from cellulose derivatives such as microcrystalline cellulose, starches, lactose, other sugars and derivatives thereof, polyols, and combinations thereof.

In some embodiments, the diluent is selected from polyols of less than 13 carbon atoms and being either in the form of a directly compressible product with a mean particle diameter of from about 100 to about 500 µm, or in the form of a powder with a mean particle diameter of less than about 100 µm. In some embodiments, these polyols are selected from mannitol, xylitol, sorbitol and maltitol, and are used in the form of a directly compressible product. In some embodiments where there are at least two soluble diluents used, one may be present in the directly compressible form and the other in the form of a powder. The proportions of directly compressible diluent and of diluent powder may be from about 99/1 to about 20/80 and preferably from about 80/20 to about 20/80.

A lubricant for the excipient layer 1 may be selected from magnesium stearate, stearic acid, sodium stearyl fumarate, polyoxyethylene glycols (e.g. micronized Macrogol 6000™), sodium benzoate, talc, glycerol behenate, and combinations thereof.

An antistatic agent for the excipient layer 1 may be selected from colloidal silica (such as the product sold under the brand name Aerosil®), precipitated silica (such as the product sold under the brand name Syloid® FP244), micronized or nonmicronized talc, and combinations thereof.

A permeabilizer for the excipient layer 1 may be selected from precipitated silica (such as such as the product sold under the brand name Syloid®), maltodextrins and β-cyclodextrins, and combinations thereof.

Sweeteners for the excipient layer 1 may be selected from aspartame, potassium acesulfame, sodium saccharinate, neohesperidine dihydrochalcone, sucralose, monoammonium glycyrrhizinate, and combinations thereof.

Suitable flavorings and colorants for the excipient layer 1 are those typically used in pharmaceutical dosage forms for the preparation of tablets.

The excipient layer 1 may make up from about 30 wt. % to about 99 wt. %, or from about 40 wt. % to about 90 wt. %, or from about 35 wt. % to about 85 wt. %, based on the total weight of the encased-pellet tablet. The weight percentage and/or thickness of the excipient layer can be modified to further adjust the API release characteristics of the tablet.

The fill weight of inner core 2 may also be modified to adjust the API release characteristics. For example, increasing the fill weight of inner core 2 while maintaining a constant thickness of excipient layer 1 will increase the percent release of the API from the encased-pellet tablet. In one embodiment, fill weights may vary from depending on the desired dosage, the type of API, tools and other known factors.

By using a cushioning agent in excipient layer 1 and/or inner core 2, damage to the pellet coating 5 as a result of compression during tableting may be reduced and the integrity of the pellet coating 5 may be preserved during tablet compression. The encased-pellet tablet of the present invention therefore can maintain the same or similar API release properties, such as controlled release, extended release, prolonged release, repeated release, or delayed release characteristics, of the encapsulated coated pellets 3.

In one embodiment, the amount of the cushioning agent in inner core 2 and/or excipient layer 1 is selected to provide particular desired API release characteristics for the encased-pellet tablet. The release profile can be adjusted in any desired manner using the present invention. For example, the release profile can be adjusted in the acid stage and/or the buffer stage to help determine where in the gastrointestinal tract API release will occur. In one embodiment, the amount of cushioning agent in inner core 2 and/or excipient layer 1 can be adjusted to attenuate the percent release of the API under acidic conditions, which may be particularly useful for enterically coated pellets containing the API and may also be important for other types of modified release coated pellets.

Incorporation of the cushioning agent in excipient layer 1 has been found to have a greater effect on the attenuation of the percent release of API under acidic conditions, relative to incorporation of the cushioning agent in the inner core 2. Under some circumstances, an additive effect on attenuation of percent release of API under acidic conditions can be achieved by incorporation of cushioning agent in both inner core 2 and excipient layer 1.

The percent release in the buffer stage follows similar trends as in the acid stage. The cushioning effect of the cushioning agent is more pronounced in the buffer stage and, as a result, lesser amounts of cushioning agent may be needed to adjust the API release profile in the buffer stage than would be needed to adjust the API release profile in the acid stage.

In another aspect, the present invention provides a method for making the encased-pellet tablet describe herein. The method may use, for example, the apparatus described in U.S. Pat. No. 7,581,941 B2. More particularly the method comprises the steps of:
 (i) compressing an excipient material into a first layer;
 (ii) compressing coated pellets 3 on said first layer to form an inner core on said first layer; and
 (iii) compressing additional excipient material with a compression force from 2 kN to 20 kN around an exposed portion of said inner core thereby surrounding said inner core with excipient material. This final compression step (iii) completes the process of surrounding inner core 2 with excipient layer 1.

The compression force used for making the encased-pellet tablet is from about 0.1 kN to about 3 kN for the first two layers, and from about 2 kN to about 20 kN, or from about 4 kN to about 15 kN, or from about 5 kN to about 12 kN, or from about 7 kN to about 10 kN for the final layer. The composition of the pellet coated tablet made by the method of the present invention is as described above.

In some embodiments, the step (ii) of the method comprises mixing the coated pellets 3 with one or more of cushion agent, a distintegrant, a plasticizer, a binder, a diluent, and an antistatic agent and compressing the mixture to form the inner core 2.

The cushioning agent that may be used in the method is selected from polyhydroxyl compounds, including polyoxyalkylene compounds having at least two hydroxy groups in the monomer molecule. Examples of cushioning agent are polyethylene glycols, polypropylene glycols, polytetramethylene glycols, polybutylene glycols, polybutadiene diols and triols, low molecular weight hydroxy-containing polyesters, hydroxy-containing polyester amides, polyalkylene ether glycol compounds, hydroxy-containing oils, including tongue oil and their alkyl modifications.

EXAMPLES

Example 1

Figure 5:
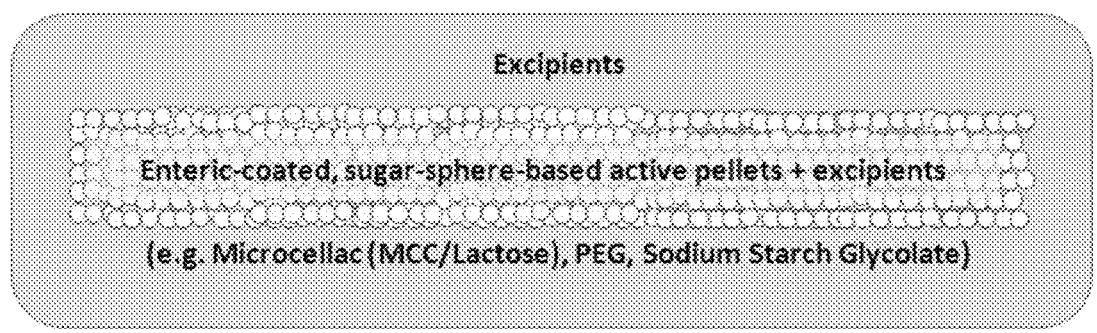
FIG. 5 is a schematic representation of an encased-pellet tablet according to an embodiment of the invention employing Microcellac® 100, PEG 6000, and sodium starch glycolate in the outer excipient layer.

Encased-pellet tablets according to the present invention were made using the OSDrC® Optidose™ technology. For this process, a Carver press was used to manually produce the tablets. The inner and outer diameters of the customized OSDrC® round punch were set to have at least a 2-mm difference. The excipient layer 1 contained Microcellac® 100 (25 wt. % microcrystalline cellulose/75 wt. % lactose monohydrate), polyethylene glycol (PEG 6000), and sodium starch glycolate (FIG. 5). The amount of API in the inner core was 100 mg. The cushioning agent was PEG 6000, and it was added to the inner core 2 and/or excipient layer 1, in the amounts shown in Table 1. The tablet compression force used to produce these tablets is also indicated in Table 1.

TABLE 1

Tablets with different amount of PEG.

| Tablet | PEG in Inner Layer (wt. %) | PEG in Excipient Layer (wt. %) | Tablet Compression Force (kN) |
|---|---|---|---|
| 1 | 0 | 0 | 2.5 |
| 2 | 0 | 0 | 5 |
| 3 | 0 | 5 | 5 |
| 4 | 0 | 10 | 5 |
| 5 | 5 | 0 | 5 |
| 6 | 10 | 0 | 5 |
| 7 | 5 | 5 | 5 |
| 8 | 10 | 5 | 5 |

Figure 2:
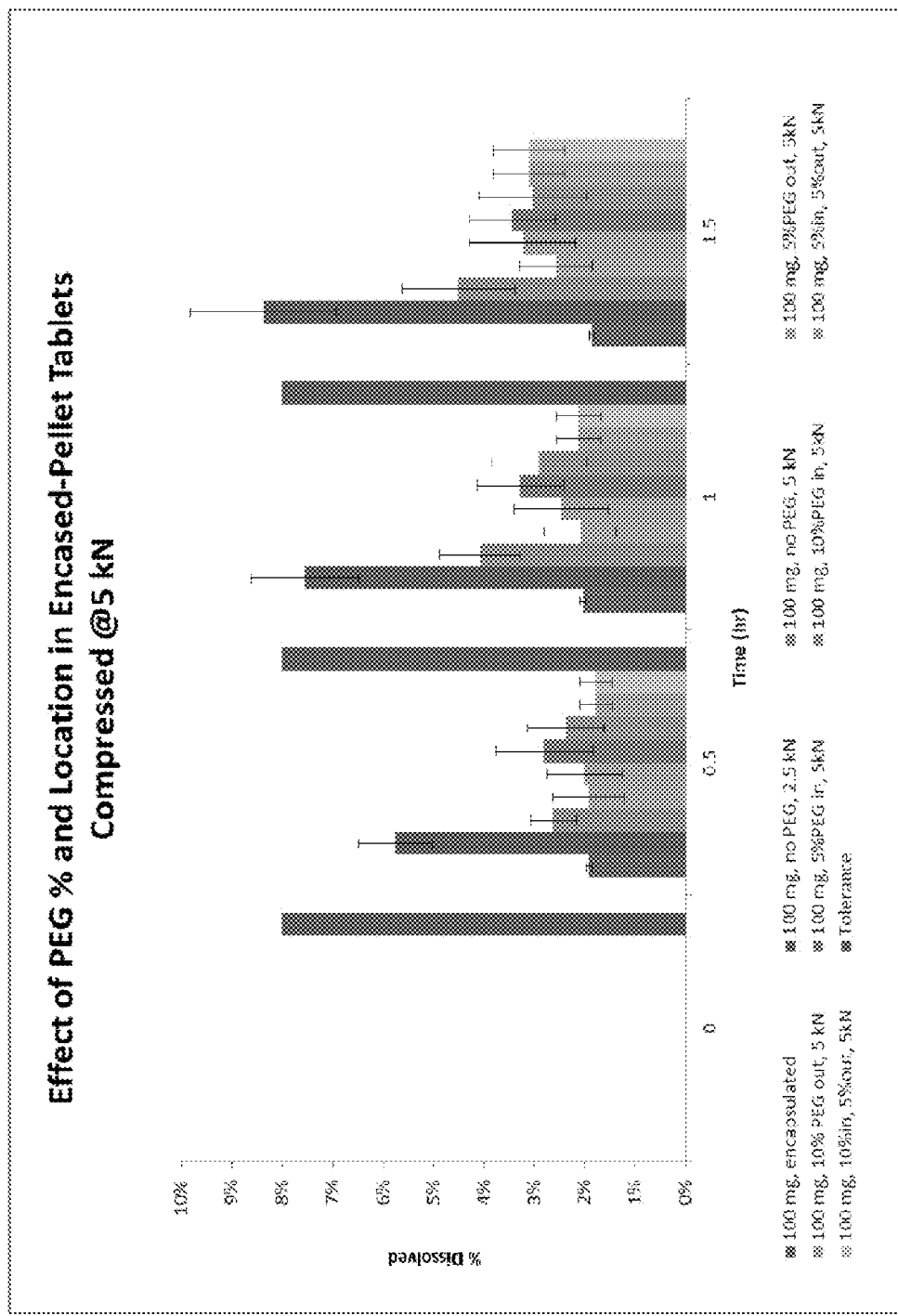
FIG. 2 is a bar chart showing release profiles in 0.1N HCl over time for the encased-pellet tablets prepared by the method of Example 1.

Coated pellets (manually encapsulated pellets), without being compressed into a tablet, were used as a control for a release assay (labeled "encapsulated" in FIG. 2). The data on "Tolerance" in FIG. 2 indicates the maximum amount of % API release as indicated by the official United States Pharmacopeia (USP) monograph, which is 8%.

The API release assay was performed in accordance with USP-NF (United States Pharmacopeia and The National Formulary) guidelines. The percentages of API release at the acid stage (0.1 N hydrochloric acid) were recorded for the produced tablets and control at 0.5, 1 and 1.5 hours, respectively (FIG. 2). In FIG. 2, the term "out" indicates that the polyethylene glycol (PEG) cushioning agent was added to the excipient layer 1 and the term "in" indicates that the PEG cushioning agent was added to the inner core 2.

For the control, the manually encapsulated pellets released about 2% of the API at 30 minutes, 1 hour, and 1.5 hours. The tablet without the PEG (2.5 kN compression force, Tablet 1) released significantly more API into the acid solution, for example, about 5.8% at 30 minutes, about 7.6% at 1 hour, and about 8.4% at 1.5 hours. The other tablet, also prepared without PEG (5 kN compression force, Tablet 2) also released more API into the acid solution than the control, for example, about 2.6% at 30 minutes, about 4.1% at 1 hour, and about 4.5% at 1.5 hours. The results for these two tablets indicate that the tablet compression force, even as little as 2.5 kN, could potentially cause damage to the pellet coating 5 thereby increasing the percent release of the API in the first 1.5 hours.

For the tablets with PEG cushioning agent added to excipient layer 1, it was observed that the addition of 5 wt. % PEG to excipient layer 1 reduced the amount of API released at 30 minutes and 1 hour to levels similar to the control, e.g. about 2%, with the release rate only rising slightly to about 2.6% at 1.5 hours. There was no significant difference in the release rates observed between tablets containing 5 wt. % and 10 wt. % PEG cushioning agent in excipient layer 1.

FIG. 2 shows a trend that addition of PEG cushioning agent to excipient layer 1 attenuates API release more effectively than addition of PEG to inner core 2. Addition of PEG to inner core 2 alone did not seem to significantly attenuate the percent release of API. When 5 wt. % PEG was added to both excipient layer 1 and inner core 2 and tablets were made by compression at 5 kN, no additional effects were observed in comparison to addition of PEG cushioning agent to excipient layer 1 only.

This example shows that adding PEG cushioning agent to excipient layer 1 in amounts of 5 wt. % to 10 wt. %, based on the total weight of the excipient layer, attenuated API release in the acid stage. Besides the cushioning effect provided by the addition of PEG to the excipient layer 1, PEG may also decrease the permeability making it more difficult for dissolution media to penetrate through the excipient layer 1.

Example 2

In this example encased-pellet tablets according to the present invention were also made using the OSDrC® Optidose™ technology. The inner and outer diameters of the customized OSDrC® round punch were set to be at least 2 mm different. A Carver press was used to manually produce the tablets. Excipient layer 1 contained Microcellac® 100 (25 wt. % microcrystalline cellulose/75 wt. % lactose monhydrate), polyethylene glycol (PEG 6000), and sodium starch glycolate (FIG. 5). The amount of API in the inner core was 100 mg. The PEG cushioning agent was added only to excipient layer 1, in the amounts shown in Table 2. No PEG was added to the pellet coating. The tablet compression force used in making the tablets varied, as shown in Table 2.

TABLE 2

Tablets with different amount of PEG and compression forces

| Tablet | PEG in Excipient Layer (wt. %) | Tablet Compression Force (kN) |
|---|---|---|
| 9 | 0 | 5 |
| 10 | 0 | 10 |
| 11 | 0 | 15 |
| 12 | 5 | 5 |
| 13 | 5 | 10 |
| 14 | 5 | 15 |
| 15 | 10 | 5 |
| 16 | 10 | 10 |
| 17 | 10 | 15 |

Figure 3:
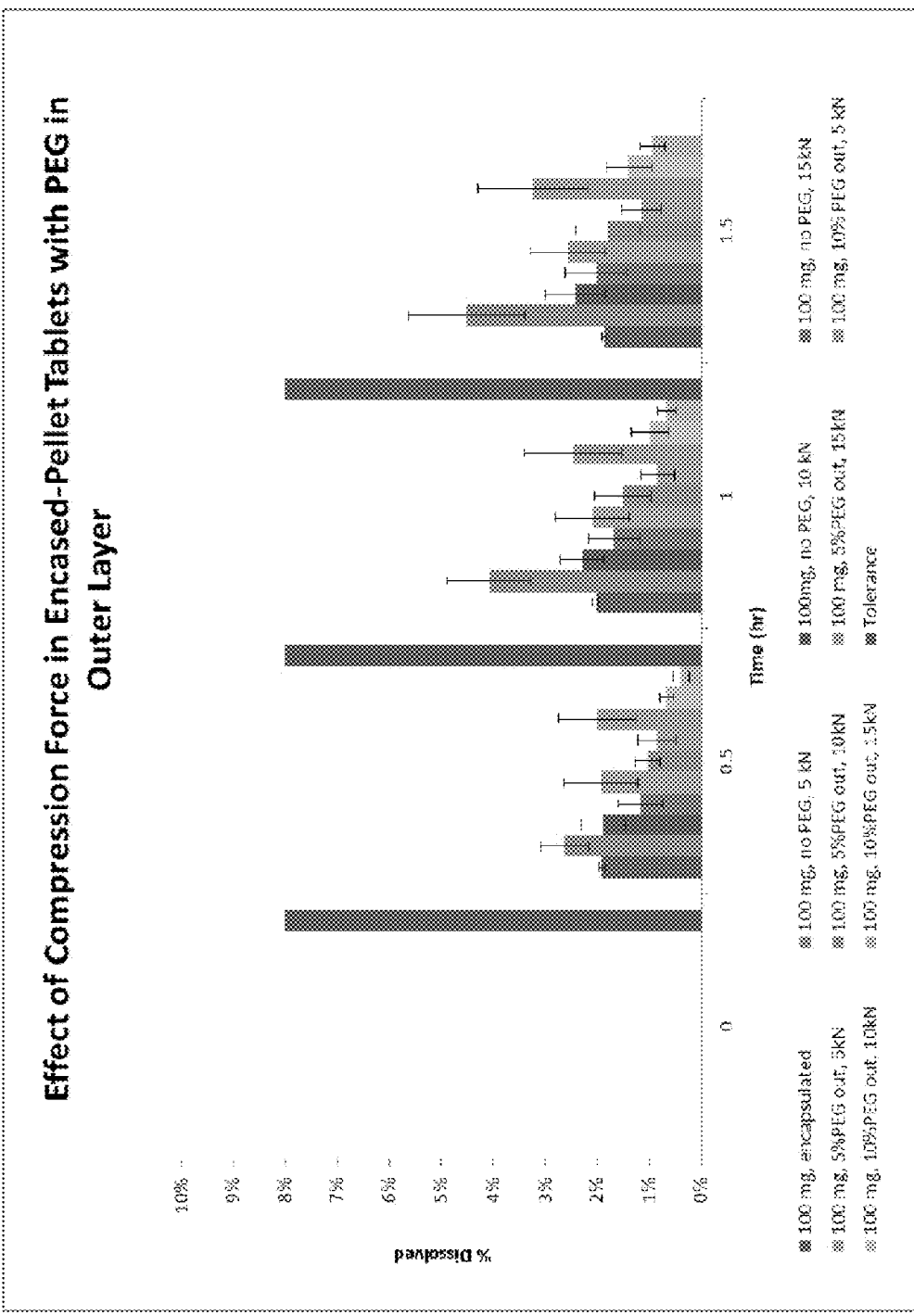
FIG. 3 is a bar chart showing release profiles in 0.1N HCl over time for encased-pellet tablets prepared in Example 2.

Coated pellets (manually encapsulated pellets), without being compressed into a tablet, were used as control for a release assay (labeled "encapsulated" in FIG. 3). The data on "Tolerance" indicates the maximum amount of % API release as indicated by the official United States Pharmacopeia (USP) monograph, which is 8%.

The API release assay was performed following the same procedure as Example 1. In FIG. 3, the term "out" means the PEG cushioning agent was added to excipient layer 1.

The results of the release assay are shown in FIG. 3. Regardless of whether PEG was added, the percent release of API decreased as the compression force increased (see FIG. 3). As the tablets and coated pellets were compressed using greater force, the pellets tended to agglomerate together and the tablets became harder, thus minimizing the surface area exposed to the dissolution media in the release assay.

For this particular example, at a compression force of 5-10 kN, the tablet appeared to have the desirable hardness. At a compression force of 15 kN, tablet hardness may be too high (the tablet released only about 1% of the API, about half of the amount released by the control).

Example 3

One objective of the present invention is to provide a percent release of API similar to that of the coated pellets (control), in both the acid and buffer stages.

Encased-pellet tablets according to the present invention were made using the OSDrC® Optidose™ technology. A Carver press was used to manually produce the tablets. The inner and outer diameters of the customized OSDrC® round punch were set to have at least a 2-mm difference. Excipient layer 1 contained Microcellac® 100 (25 wt. % microcrystalline cellulose/75 wt. % lactose monohydrate), polyethylene glycol (PEG 6000), and sodium starch glycolate (FIG. 5). The amount of API in the inner core was 150 mg. The PEG cushioning agent was added to inner core 2 and/or excipient layer 1, in the amounts shown in Table 3. The tablet compression force used to produce these tablets is also indicated in Table 3.

TABLE 3

Tablets with different amount of PEG.

| Tablet | PEG in Inner Layer (wt. %) | PEG in Excipient Layer (wt. %) | Tablet Compression Force (kN) |
|---|---|---|---|
| 18 | 0 | 0 | 5 |
| 19 | 0 | 10 | 5 |
| 20 | 10 | 0 | 5 |
| 21 | 10 | 10 | 5 |

Figure 4:
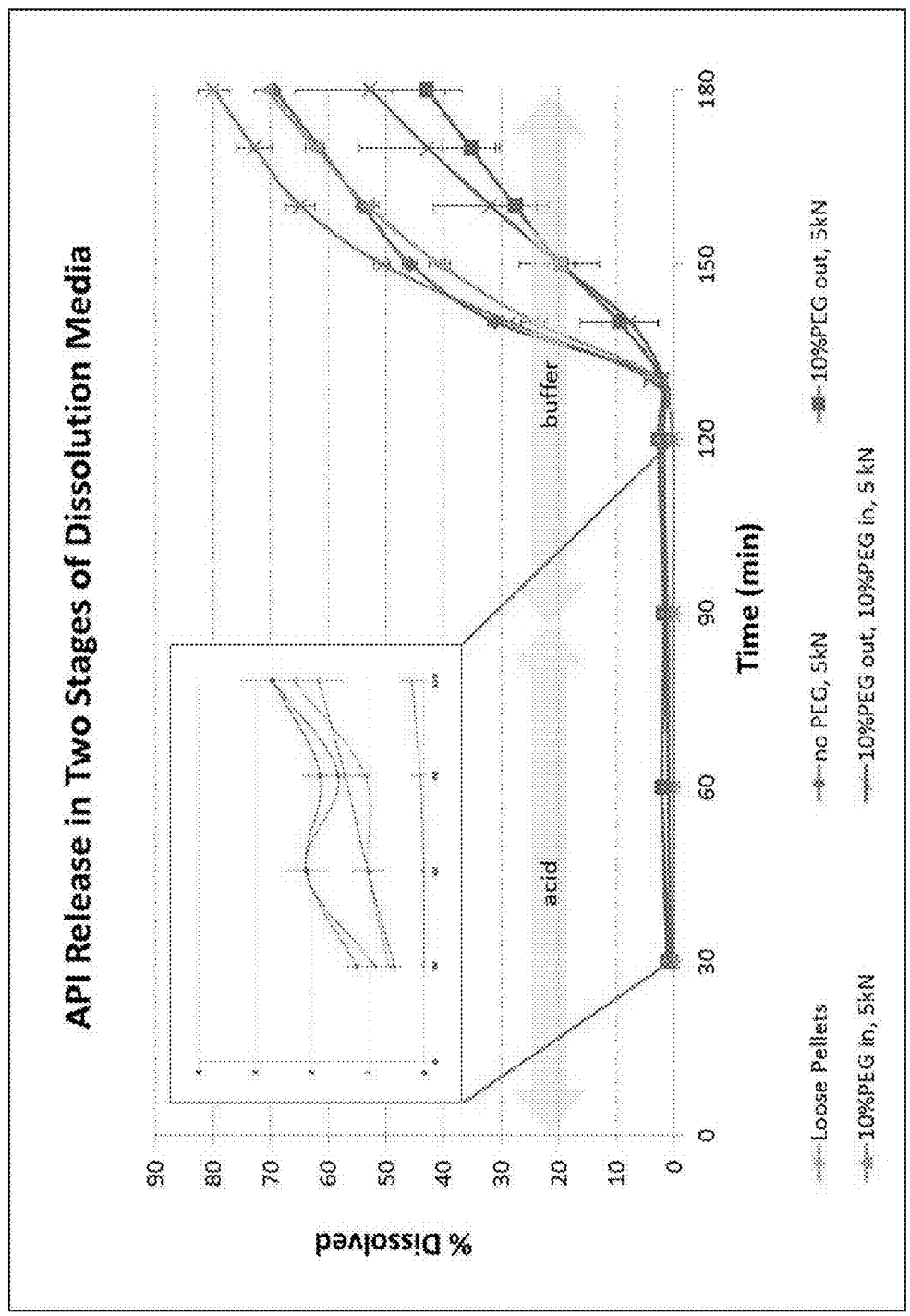
FIG. 4 is a scatter graph showing release profiles over time, both in the acid (0.1N HCl) and buffer (pH 5.5) stages, for the encased-pellet tablets prepared in Example 3.

Loose coated pellets, without being compressed into a tablet, were used as a control for a release assay (labeled "loose pellets" in FIG. 4).

The API release assay was performed in 0.1N HCl for 120 minutes and crossed-over to pH 5.5 buffer for additional 60 minutes, with a total dissolution period of 180 minutes. The term "out" indicates that the PEG was added to the excipient layer 1, and the term "in" indicates that the PEG was added to the inner core 2.

In the acid stage (shown in the insert in the left corner of FIG. 4), the loose pellets released less than 1% of the API at 120 minutes. Without the addition of PEG, the tablets released, on average about 2.1% of the API at 60 minutes and about 2.7% of the API at 120 minutes. The tablets made with the addition of PEG in the excipient layer 1 also showed a similar release profile.

The tablets made with addition of PEG either in excipient layer 1, inner core 2, or both excipient layer 1 and inner core 2, at a compression force of 5 kN, had similar release profiles, and these tablets released between 1.9% to 2.7% of the API at 120 minutes.

Although the API release of the tablets was still less than the maximum amount of percent API release (tolerance) as indicated by the official United States Pharmacopeia (USP) monograph, i.e. 8% API, a greater release of API in the acid stage may jeopardize product performance during stability tests. The addition of the cushioning agent, PEG, has been shown to reduce the API release in the acid stage and thus would also be expected to improve results obtained in stability tests.

In addition, it is also important that API be released in the buffer stage in a similar manner to the control.

For the buffer stage (see FIG. 4, "buffer" region), the release profiles of the tablets made with no PEG and with 10 wt. % PEG cushioning agent in the inner core 2 were almost identical. The release profile of a tablet produced with 10% PEG cushioning agent in the excipient layer 1 showed a similar release profile to the tablets made with addition of PEG in both excipient layer 1 and inner core 2 in dissolution periods of 130 and 180 minutes.

The release profile in the buffer stage (FIG. 4) was observed to be similar to that in Example 2 and FIG. 2. FIG. 4 shows a trend that the addition of PEG cushioning agent to the excipient layer 1 attenuates API release more effectively than addition of PEG to the inner core 2. Addition of PEG to the inner core 2 alone did not seem to significantly attenuate the percent release of API. When 10 wt. % PEG was added to both the excipient layer 1 and the inner core 2 and tablets were made by compression at 5 kN, no additional effects were observed in comparison to addition of PEG cushioning agent to only the excipient layer 1.

In the cross-over dissolution study, there was no burst effect observed in the buffer stage. Thus, the data suggested that the pellets were well protected and that the coating was minimally compromised during the compression process.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, composition and arrangement of parts within the principles of the invention to the full extent indicated by the broad general meanings of the terms in which the appended claims are expressed.

What is claimed is:

1. An encased-pellet tablet for an active pharmaceutical ingredient, comprising:
   an inner core including an excipient matrix and a plurality of individually coated pellets containing at least one active pharmaceutical ingredient coated with a pellet coating, and
   an excipient layer completely surrounding the inner core including all of the coated pellets of the inner core,
   wherein the excipient layer contains from about 1 wt. % to about 20 wt. % of at least one cushioning agent selected from polyhydroxyl compounds, based on the total weight of the excipient layer.

2. The encased-pellet tablet of claim 1, wherein the inner core comprises two or more different coated pellets.

3. The encased-pellet tablet of claim 2, wherein the two or more different coated pellets have different pellet coatings that provide different active pharmaceutical ingredient release profiles to the coated pellets.

4. The encased-pellet tablet of claim 2, wherein the two or more different types of coated pellets comprise pellets with different active pharmaceutical ingredients.

5. The encased-pellet tablet of claim 1, wherein the pellet coating has at least one function selected from the group consisting of taste masking, odor masking, stabilization of the active pharmaceutical ingredient, improving processability of the active pharmaceutical ingredient, improving the flow behavior of the active pharmaceutical ingredient, decreasing the hygroscopicity of the active pharmaceutical ingredient, guaranteeing and improving the chemical and/or mechanical stability of the active pharmaceutical ingredient, modifying the release of the active pharmaceutical ingredient from the coated pellet, modifying the API bioavailability, and coloring.

6. The encased-pellet tablet of claim 1, wherein the at least one cushioning agent comprises from about 2 wt. % to about 18 wt. % of the excipient layer.

7. The encased-pellet tablet of claim 1, wherein the at least one cushioning agent comprises from about 4 wt. % to about 18 wt. % of the excipient layer.

8. The encased-pellet tablet of claim 1, wherein the at least one cushioning agent comprises from about 5 wt. % to about 15 wt. %, or from about 7 wt. % to about 12 wt. %, or from about 4 wt. % to about 11 wt. %, of the excipient layer.

9. The encased-pellet tablet of claim 1, wherein the excipient matrix of the inner core comprises at least one component selected from cushioning agents, disintegrants, plasticizers, binders, diluents, and antistatic agents.

10. The encased-pellet tablet of claim 1, wherein the at least one cushioning agent is selected from polyethylene glycols, polypropylene glycols, polytetramethylene glycols, polybutylene glycols, polybutadiene diols and triols, low molecular weight hydroxy-containing polyesters, hydroxy-containing polyester amides, polyalkylene ether glycol compounds, and hydroxy-containing oils.

11. The encased-pellet tablet of claim 1, wherein the at least one cushioning agent comprises polyethylene glycol.

12. The encased-pellet tablet of claim 1, wherein the excipient layer comprises a polymer selected from ethylcellulose, methylcellulose, hydroxypropylmethyl cellulose, cellulose acetate phthalate, polymers of methacrylic acid and methacrylic acid esters, microcrystalline cellulose, polysaccharides such as lactose, and combinations thereof.

13. The encased-pellet tablet of claim 1, wherein the excipient layer comprises one or more excipients selected from the group consisting of a disintegrant, a swelling agent, a diluent, a lubricant, an antistatic agent or a glidant, a permeabilizer, a sweetener, a flavoring agent, and a colorant.

14. The encased-pellet tablet of claim 1, wherein the excipient matrix of the inner core comprises at least one cushioning agent selected from polyhydroxyl compounds.

15. The encased-pellet tablet of claim 14, wherein the at least one cushioning agent in the excipient matrix of the inner core comprises a cushioning agent selected from polyethylene glycols, polypropylene glycols, polytetramethylene glycols, polybutylene glycols, polybutadiene diols and triols, low molecular weight hydroxy-containing polyesters, hydroxy-containing polyester amides, polyalkylene ether glycol compounds, and hydroxy-containing oils.

16. The encased-pellet tablet of claim 14, wherein the at least one cushioning agent in the excipient matrix of the inner core comprises polyethylene glycol.

17. The encased-pellet tablet of claim 1, wherein the at least one cushioning agent in the excipient matrix of the inner core has a weight percentage of from about 1% to about 20%, or from about 2% to about 18%, or from 4% to about 18%, or from 5% to about 15%, or from 7% to about 12%, or from 4% to about 11% of the total weight of the inner core.

18. A method for manufacturing an encased-pellet tablet, comprising the steps of:
   (i) compressing an excipient material with a compression force from about 0.1 kN to 3 kN to form a first layer of excipient material;

(ii) compressing a excipient matrix and a plurality of individually coated pellets containing an active pharmaceutical ingredient on said first layer with a compression force from about 0.1 kN to 3 kN to form an inner core of said excipient matrix and said coated pellets on said first layer; and (iii) compressing additional excipient material with a compression force from 2 kN to 20 kN around an exposed portion of said inner core thereby completely surrounding said inner core including all of the coated pellets of the inner core with said excipient material from steps (i) and (iii).

19. The method of claim 18, wherein the compression force for step (iii) is from about 4 kN to about 15 kN.

20. The method of claim 18, wherein the compression force for step (iii) is from about 5 kN to about 12 kN.

21. The encased-pellet table of claim 1, wherein the excipient layer comprises at least 40 wt. %, based on the total weight of the encased pellet-tablet.

* * * * *